United States Patent [19]

Chavkin

[11] Patent Number: 4,534,960

[45] Date of Patent: Aug. 13, 1985

[54] MENTHOLATED ORAL COMPOSITION

[75] Inventor: Leonard Chavkin, Westfield, N.J.

[73] Assignee: Warren Glen Products, Inc., Bloomsbury, N.J.

[21] Appl. No.: 599,641

[22] Filed: Apr. 12, 1984

[51] Int. Cl.$^3$ .......................... A61K 7/16; A61K 7/26
[52] U.S. Cl. ...................................... 424/49; 424/48; 514/729; 514/777
[58] Field of Search .................................. 424/49–58, 424/343, 361

[56] References Cited

U.S. PATENT DOCUMENTS

| 4,279,888 | 7/1981 | Suganuma et al. | 424/50 |
| 4,383,987 | 5/1983 | Kiozpeoplou | 424/49 |
| 4,407,788 | 10/1983 | Kiozpeoplou | 424/49 |
| 4,408,041 | 10/1983 | Hirao et al. | 424/48 |
| 4,435,380 | 3/1984 | Pader | 424/49 |
| 4,448,778 | 5/1984 | Lynch | 424/260 |
| 4,457,921 | 7/1984 | Stroz et al. | 424/48 |
| 4,466,954 | 8/1984 | Ichikawa et al. | 424/50 |
| 4,469,673 | 9/1984 | Iioka et al. | 424/50 |

OTHER PUBLICATIONS

Jacobs Am. Perf. 61:469–471 Jun. 1953, Flavoring Mouthwashes.
Jacobs Am. Perf. 61:389–939 May 1953, How to Flavor Toothpastes.

*Primary Examiner*—Shep K. Rose
*Attorney, Agent, or Firm*—Omri M. Behr

[57] ABSTRACT

There is provided a mentholated composition for use in the oral cavity which contains menthol in the presence of hydrogenated glucose syrup. The presence of said syrup permits the use of substantially higher concentrations of menthol than was heretofore possible due to the irritant properties of menthol at such elevated concentrations.

3 Claims, No Drawings

MENTHOLATED ORAL COMPOSITION

BACKGROUND OF THE INVENTION

Menthol is commonly used as an analgesic and anesthetic agent in early treatment of sore throats and its vapors are known to have decongestant action as well as possessing antitussive properties.

Products for the foregoing purposes containing menthol have been well known for many years. Unfortunately menthol, above 0.1% by weight, acts as an irritant to the mucous membranes and, notwithstanding the desirability of utilizing higher concentrations for its physiological effect, achievement of concentrations above the 0.1% level has heretofore not been possible because of such concentrations could not be tolerated because of the "burning" sensation caused thereby. Such concentrations of 0.1% while sufficient to provide flavor and aromatic effect are insufficient to have any substantial decongestant action.

In studies published by an FDA advisory review panel, concentrations of 0.25 to 1% in aqueous solution have been recommended in the treatment of hemmorrhoids, a condition affecting rectal mucous tissue. Thus, it is clear from these studies that concentrations of menthol of the order of 0.25 to 1% are considered physiologically safe provided that the sensations caused thereby can be tolerated by the patient. These concentrations represent an increase of concentration of between 2.5 and 10-fold that which was heretofore available.

In studies relating to the provision of noncarieogenic sweetners utilizable in oral medicinal products, it has been found that that hydrogenated glucose syrup may be utilized in place of more traditional sweeteners. A substantial number of such syrups are available, suitably they are prepared by enzymatic hydrolysis of food starch followed by hydrogenation of the keto groups of the constituent sugars to the corresponding alcohol. The actual reduced sugar composition of these syrups will vary depending upon their origin, however, their common characteristic is that they are substantially devoid of oxo groups and contains a high proportion, suitably at least 75% of maltilol.

SUMMARY OF THE INVENTION

It has been found that by compounding hydrogenated glucose syrups with menthol, it is possible to raise the concentration of menthol which is orally acceptable without discomfort to levels of between 0.25 and 1% by weight. It thus becomes possible to utilize the decongestant properties of menthol in mouthwashes and mouth sprays, a use not heretofore possible since decongestively effective concentrations were not acceptable by patients.

DESCRIPTION OF THE PREFERRED EMBODIMENTS

The compositions of the present invention which are orally acceptable are characterized by the presence therein of between 0.25 and 1% by weight of menthol in the presence of between 10 and 50% by weight of hydrogenated glucose syrups. The compositions may, for example, be decongestant mouthwashes/gargles or oral cavity sprays for the relief of symptoms of the common cold. The remaining constituents of these compositions can be regarded as substantially conventional. That is to say, the compositions are water based and contain ethanol, flavoring, glycerine and emulsifying agents. While these components are desirable the invention should not be considered as being limited thereby. The substitution of other components well known to those skilled in the art therefore, should be considered to be within the scope of the present invention.

The compositions of the present invention have been utilized in human in vivo testing, all respondents have noted a favorable and immediate decongestant action provided by the formulation. Such an effect is highly desirable because it provides decongestant action without the undesirable drawing engendered by a large number of decongestant materials, particularly of the antihistamine type.

EXAMPLE I

Decongestant Mouthwash/Gargle for Colds Symptoms

|  | % by Weight |
| --- | --- |
| Menthol | 0.4 |
| Lycasin 80:55 | 20.0 |
| Pluronic F127 | 1.5 |
| Glycerin | 10.0 |
| Flavor | 0.2 |
| Ethanol | 15.0 |
| Purified Water | 52.9 |
|  | 100.0% |

In accordance with the above formulation between 0.25 and 0.5% (w/w) of menthol may be used.

The mouthwash is utilized undiluted in aliquots of 10 to 15 ml, from 4 to 6 times per day.

EXAMPLE II

Oral Cavity Spray for Colds Symptoms

|  | % by Weight |
| --- | --- |
| Menthol | 0.8 |
| Lycasin 80:55 | 40.0 |
| Pluronic F127 | 2.0 |
| Glycerin | 20.0 |
| Flavor | 0.2 |
| Ethanol | 15.0 |
| Purified Water | 22.0 |
|  | 100.0% |

In accordance with the above formulation there may be used between 0.6 and 1% by weight of menthol.

The spray may be used at between about 1 and about 3 ml. of spray per application from 4 to 6 times per day.

I claim:

1. In a method of gargling with mouth wash or mouth sprays containing menthol, the improvement which comprises raising the concentration of menthol which is orally acceptable without discomfort which consists of the step of contacting the mucous membranes of the oral cavity with
    from about 0.25 to about 1% by weight of menthol and from about 10 to 50% by weight of hydrogenated glucose syrup.
2. A method of claim 1 wherein the mouth wash composition comprises form about 0.25 to about 0.6% by weight of menthol and
    about 15 to about 25% by weight of hydrogenated glucose syrup.
3. A method of claim 2 wherein the oral cavity spray comprises from
    about 0.6 to about 1% by weight of menthol
    and from about 30 to about 50% by weight of hydrogenated glucose syrup.

* * * * *